(12) United States Patent
Ota et al.

(10) Patent No.: US 9,320,770 B2
(45) Date of Patent: Apr. 26, 2016

(54) BLOOD VESSEL MATURATION, NORMALIZATION OR STABILIZATION AGENT AND WRINKLE PREVENTER/IMPROVER

(75) Inventors: Masahiro Ota, Yokohama (JP); Koji Kobayashi, Yokohama (JP); Ken Kusakari, Yokohama (JP); Makoto Tsunenaga, Yokohama (JP); Nobuyuki Takakura, Toyonaka (JP)

(73) Assignee: Shiseido Company, Ltd., Tokyo (JP)

( * ) Notice: Subject to any disclaimer, the term of this patent is extended or adjusted under 35 U.S.C. 154(b) by 1082 days.

(21) Appl. No.: 12/736,316

(22) PCT Filed: Mar. 31, 2009

(86) PCT No.: PCT/JP2009/056709
§ 371 (c)(1),
(2), (4) Date: Sep. 29, 2010

(87) PCT Pub. No.: WO2009/123211
PCT Pub. Date: Oct. 8, 2009

(65) Prior Publication Data
US 2011/0014307 A1 Jan. 20, 2011

(30) Foreign Application Priority Data
Mar. 31, 2008 (JP) ................................. 2008-093363

(51) Int. Cl.
*A61K 36/54* (2006.01)
*A61K 8/97* (2006.01)
*A61Q 19/08* (2006.01)

(52) U.S. Cl.
CPC . *A61K 36/54* (2013.01); *A61K 8/97* (2013.01); *A61Q 19/08* (2013.01)

(58) Field of Classification Search
USPC ........................................................ 424/739
IPC ...................................................... A61K 36/54
See application file for complete search history.

(56) References Cited

U.S. PATENT DOCUMENTS

| 2001/0002257 | A1* | 5/2001 | Stolz ......................... | A61K 8/44 424/401 |
| 2005/0266064 | A1* | 12/2005 | McCarthy .................... | 424/450 |
| 2005/0287233 | A1* | 12/2005 | Mae .......................... | A21D 2/36 424/739 |
| 2006/0127505 | A1* | 6/2006 | Haines ....................... | A61K 31/015 424/729 |
| 2006/0275515 | A1* | 12/2006 | Ovadia ........................ | A61L 2/16 424/739 |
| 2008/0233209 | A1* | 9/2008 | Fogg-Johnson .............. | A61K 31/336 424/655 |
| 2009/0203649 | A1* | 8/2009 | Kato et al. ..................... | 514/100 |
| 2010/0055138 | A1* | 3/2010 | Margulies et al. ............. | 424/401 |

FOREIGN PATENT DOCUMENTS

| DE | 10017865 A1 | 10/2001 |
| FR | 2791255 A1 | 9/2000 |
| JP | 11-106336 A | 4/1999 |
| JP | 2000-159627 A | 6/2000 |
| JP | 2005-008539 A | 1/2005 |
| JP | 2005-015450 A | 1/2005 |
| JP | 2007-261996 A | 10/2007 |
| KR | 10-0213897 B1 | 8/1999 |
| KR | 2003024284 A * | 3/2003 |
| KR | 2003024284 A * | 3/2006 |
| WO | WO 02/47701 A1 | 6/2002 |

OTHER PUBLICATIONS

Viable Herbal Solution (see cited website of www.web.archive.org/web/20000124113842//http://viable-herbal.com/herbology1/herbs42, copyrighted 1996,1997,1998,1999,2000, pp. 1-3).*
Traditional Chinese Drug Research & Clinical Phamacology, May 2007, 18(3):249-259 (see Transmittal Letter for concise explanation of relevance).
International Search Report mailed Jun. 30, 2009, in PCT/JP2009/056708, 3 pages.
Bae et al., "Screening of angiogenesis inhibitors from Korean plants (I)," Korean J. Pharmacog., 2000, 31(3):320-324.
Cao et al., "Cinnamon extract and polyphenols affect the expression of tristetraprolin, insulin receptor, and glucose transporter 4 in mouse 3T3-L1 adipocytes," Archives of Biochemistry and Biophysics, 2007, 459:214-222.
Kwon et al., "Synthesis and Biological Activity of Cinnamaldehydes as Angiogenesis Inhibitors," Bioorganic & Medicinal Chemistry Letters, 1997, 7(19):2473-2476.
Key Attributes of TKDL, 1996, Suryaprabhagutika, retrieved on Jan. 4, 2012, 4 pages, with English translation, 4 pages.

* cited by examiner

*Primary Examiner* — Chris R Tate
(74) *Attorney, Agent, or Firm* — Foley & Lardner LLP

(57) ABSTRACT

A vascular maturation, normalization or stabilization agent, or a Tie-2 activation agent, is provided comprising an extract derived from a plant belonging to the genus *Cinnamomum*.

4 Claims, 6 Drawing Sheets

BLOOD VESSEL MATURATION, NORMALIZATION OR STABILIZATION AGENT AND WRINKLE PREVENTER/IMPROVER

TECHNICAL FIELD

The present invention relates to a blood vessel maturation, normalization or stabilization agent, a Tie2 (Tyrosine Kinase with Ig and EGF Homology Domain 2) activation agent and a wrinkle preventer/improver composed of an extract derived from a plant belonging to the genus *Cinnamomum*, and particularly a plant of the species *Cinnamomum cassia* Blume.

BACKGROUND ART

In blood vessels, vascular smooth muscle cells and pericytes, which are generically referred to as vascular mural cells, adhere to vascular endothelial cells from the outer surface of the vascular endothelial cells either directly or via the extracellular matrix. The ratios of adhesion of endothelial cells and parietal cells differ depending on the size of the vessel diameter, and in large vessels, multiple of layers of mural cells line a single layer of endothelial cells, in medium and small vessels, a single parietal cell lines a single endothelial cell, while in narrow-diameter vessels, a single parietal cell adheres to a plurality of endothelial cells. In this manner, lining of vascular endothelial cells by parietal cells is important for the structural "maturation" process of blood vessels. In addition, the formation of focal adhesion between endothelial cells by adhesion between vascular endothelial cells so that intravascular environmental factors (cellular and humoral factors) do not easily leak outside blood vessels is important for the functional "maturation" process of blood vessels. Moreover, blood vessels regulate blood flow so that oxygen and nutrients adequately reach all tissues by increasing blood flow through dilation of the lumen in response to demands for oxygen and nutrients by tissues, and particularly when there is a shortage thereof. In other words, the process by which the vessel lumen is controlled to be large, medium or small through structural stabilization by controlling permeability as a result of vascular endothelial cells forming focal adhesion and inducing structural stabilization due to the accompanying lining of parietal cells with vascular endothelial cells is defined as "vascular maturation".

In addition, vessels having impaired vessel structures are formed in various disease states, and immature vessels are formed in which adhesion between endothelial cells is inhibited or adhesion of parietal cells to endothelial cells is deficient. This leads to unregulated increases in vascular permeability, resulting in abnormalities in exchanges between humoral factors and cells in tissue and blood vessels. Increased permeability results in the formation of tissue edema, which in turn causes impaired tissue function and leads to inflammation due to unregulated infiltration of inflammatory cells. Moreover, since parietal cells inhibit vascular sprouting from existing vessels, sprouting of vessels from vessels not having parietal cells becomes excessive and unregulated vessel sprouting is induced that results in exacerbation of the disease state. This type of phenomenon is observed in diseases represented by diabetic retinopathy, tumors and inflammations. In other words, the returning of blood vessels in which vascular permeability has been impaired or abnormal blood vessels that cause unregulated vascular hyperplasia to a normal state by enhancing adhesion between endothelial cells and promoting lining of endothelial cells with parietal cells is defined as "vascular normalization". In addition, in abnormal blood vessels as described above, changes in circulatory internal and external environmental factors caused by diabetes, hyperlipemia or hypertension and the like impart damage (such as cell death) to endothelial cells and parietal cells, and are triggered by excessive increases in production of angiogenesis promoting factors caused by cancer or inflammation. When such a disease state has occurred, inhibiting damage to existing vessels and inhibiting dissociation between endothelial cells or inhibiting dissociation between endothelial cells and parietal cells is defined as "vascular stabilization". In addition, a mechanism that inhibits cell death of endothelial cells is included in this stabilization.

Angiogenesis refers to a phenomenon by which a network of new blood vessels is formed from existing vessels, and is intimately involved with diseases primarily associated with vascular lesions, such as tumors, chronic rheumatoid arthritis, diabetic retinopathy, hyperlipemia or hypertension. Following the molecular cloning of vascular endothelial growth factor (VEGF), molecules of the VEGF family and angiopoietin (Ang) family have successively been identified as factors that specifically act on blood vessel formation. VEGF and its receptors are involved in an extremely wide range of vessel formation, extending from the initial formation of blood vessels referred to as vasculogenesis to its subsequent angiogenesis. On the other hand, Ang functions in lumen formation accompanying cellular phenomena such as sprouting, branching, intussusception or pruning by vascular endothelial cells following vasculogenesis. Ang controls adhesion between vascular endothelial cells and vascular parietal cells in the manner of peripheral cells (pericytes) and vascular smooth muscle cells through a receptor-type tyrosine kinase Tie (tyrosine kinase with Ig and EGF homology domain)-2 that is expressed in vascular endothelial cells, and functions in structural stabilization of blood vessels (Experimental Medicine, Vol. 20, No. 8 (2002), pp. 52-57: Non-Patent Document 1).

Four angiopoietin isoforms, consisting of Ang-1 to Ang-4, have previously been known, and although Ang-1 and Ang-2 are present in both humans and mice, Ang-3 is only present in mice while Ang-4 is only present in humans. Ang-1 and Ang-4 secreted from parietal cells induce adhesion between endothelial cells and parietal cells accompanying stimulation of Tie-2, induction of autophosphorylation of the intracellular tyrosine kinase domain, activation of integrin, activation of focal adhesion kinase (FAK) and activation of phosphatidylinositol-3-kinase/serine-threonine kinase (PI3K/Akt). In a normal oxygen state, although adhesion between endothelial cells and parietal cells is maintained by Ang-1 and Ang-4 constantly secreted by parietal cells, when a local hypoxic state occurs, production of Ang-1 and Ang-4 antagonists in the form of Ang-2 and Ang-3 increases, thereby temporarily inhibiting activation of Tie-2 and inhibiting adhesion between endothelial cells and the parietal cells that line them. Endothelial cells then proliferate and begin sprouting angiogenesis due to dissociation of parietal cells, which leads to the formation of a new vascular network. Since Tie-2 activation induces adhesion between endothelial cells and parietal cells, it contributes to stabilization of vessel structure, while also controlling vascular permeability by promoting adhesion between endothelial cells. In addition, since activation of Tie-2 is also known to inhibit cell death of endothelial cells (Cho, C. H., Kammerer, R. A., Lee, H. J., Yasunaga, K., Kim, K. T., Choi, H. H., Kim, W., Kim, S. H., Park, S. K., Lee, G. M. and Koh, G. Y.: Designed angiopoietin-1 variant, COMP-Ang1, protects against radiation-induced endothelial cell apoptosis, Proc. Natl. Acad. Sci. U.S.A., 2004, Apr. 13, 101

(15), 5553-8: Non-Patent Document 2), blood vessels can be stabilized and normalized in response to environmental factors that damage various intracellular and extracellular vascular structures by inducing activation of Tie-2 and inhibiting blood vessel instability. In addition, by inducing activation of Tie-2 in blood vessels that have been formed by vascular endothelial cells in vascular regenerative therapy, blood vessel maturation is possible by inducing adhesion between endothelial cells and parietal cells. In addition, in diseases such as tumors or diabetic retinopathy, in which blood vessels exhibit unregulated growth as a result of parietal cells not adhering to endothelial cells, activation of Tie-2 makes it possible to normalize blood vessels by causing parietal cells to adhere to endothelial cells. In addition, according to the literature (Thurston, G., Suri, C., Smith, K., McClain, J., Sato, T. N., Yancopoulos, G. D. and McDonald, D. M.: Leakage-resistant blood vessels in mice transgenically overexpressing angiopoietin-1, Science 1999, Dec. 24, 286 (5449): Non-Patent Document 3), activation of Tie-2 has been reported to dilate vascular lumen, and in ischemic diseases occurring caused by vascular contraction or inhibition of vascular dilation, disease state can be improved through dilation of vascular lumen by activation of Tie-2.

In addition, a plurality of molecules having a coiled-coiled domain and fibrinogen-like domain, which are structural characteristics of Ang, have recently been discovered. Since these do not have the ability to bind to Tie-1 receptors or Tie-2 receptors, they are considered to constitute a group of molecules that differs from the existing Ang family, have been named angiopoietin-like protein (Angpt1), and Angpt-1, -2, -3, -4, -5, -6 and -7 have been reported. Although these Angpt1 are orphan ligands for which receptors have yet to be identified, they are expected to demonstrate various actions.

Activation of Tie-2 is also known to induce a dormant state in cells other than vascular endothelial cells. According to previous reports, activation of Tie-2 in hematopoietic stem cells has been reported to induce dormancy in the hematopoietic stem cells (Arai, F., Hirao, A., Ohmura, M., Sato, H., Matsuoka, S., Takubo, K., Ito, K., Koh, G. Y. and Suda, T.: Tie2/angiopoietin-1 signaling regulates hematopoietic stem cell quiescence in the bone marrow niche, Cell, 2004, Jul. 23, 118(2), 149-161: Non-Patent Document 4). In other words, induction of Tie-2 makes it possible to maintain survival of hematopoietic stem cells in vitro for long periods of time. In addition, according to previous reports, activation of Tie-2 is known to induce adhesion of cells to the extracellular matrix and the like by activating adhesion factors such as integrin (Takakura, N., Huang, X. L., Naruse, T., Hamaguchi, I., Dumont, D. J., Yancopoulos, G. D. and Suda, T.: Critical role of the TIE2 endothelial cell receptor in the development of definitive hematopoiesis, Immunity, 1998, Nov., 9(5), 677-86: Non-Patent Document 5). Induction of this cell adhesion is thought to enable induction of maintenance of anchorage-dependent survival in hematopoietic stem cells both in vitro and in vivo due to activation of Tie-2. Moreover, according to recent reports, expression of Tie-2 has been suggested in cancer stem cells, considered to have the highest degree of malignancy in cancer tissue and be involved in cancer relapse (Lee, O. H., Xu, J., Fueyo, J., Fuller, G. N., Aldape, K. D., Alonso, M. M., Piao, Y., Liu, T. J., Lang, F. F., Bekele, B. N. and Gomez-Manzano, C.: Expression of the receptor tyrosine kinase Tie2 in neoplastic glial cells is associated with integrin beta1-dependent adhesion to the extracellular matrix, Mol. Cancer Res., 2006, Dec., 4(12), 915-26: Non-Patent Document 6). In the same manner as activation of Tie-2 is able to cause the cell cycle of hematopoietic stem cells to enter a dormant state, proliferation of cancer stem cells can also be inhibited by activation of Tie-2 expressed in cancer stem cells.

DISCLOSURE OF THE INVENTION

Problems to be Solved by the Invention

An object of the present invention is to provide a novel vascular maturation, normalization, stabilization and Tie-2 activation (phosphorylation) agent.

Means for Solving the Problems

Behavior within skin tissue irradiated with ultraviolet B was studied in detail by the inventors of the present invention. Irradiation with ultraviolet B evoked considerable epidermal hypertrophy and skin vasculariation and caused wrinkle formation. It was found that expression of Ang-1 was significantly depressed in skin tissue subjected to such photoaging, while expression of Ang-2 was found to have increased relative to Ang-1. Moreover, the desquamated status of parietal cells from vascular endothelial cells caused by ultraviolet radiation was observed in skin tissue sections. According to these findings, adhesion between endothelial cells and parietal cells was inhibited by ultraviolet radiation, and it was suggested that a state was induced in which inhibition of Tie-2 phosphorylation, namely Tie-2 activation, was inhibited. On the basis of experiments conducted by allowing various herbal medicine extracts to act on a murine pro-B cell line, Ba/F3 transduced with full-length murine TIE2(BaF/TIE2), and human umbilical vein endothelial cells (HUVEC) extracts derived from plants belonging to the genus *Cinnamomum* were found to have action that activates Tie-2. In addition, as a result of applying cinnamon twig extract onto mouse skin in which photoaging had been evoked by irradiating with ultraviolet B, ameliorative action was specifically indicated by applying this extract. Accordingly, this extract was found to improve and promote adhesion between endothelial cells and parietal cells due to phosphorylation of Tie-2, enable the formation of a stable vascular structure, and in turn, enable recovery of UVB-induced skin damage and wrinkle formation, thereby leading to completion of the present invention.

Thus, the present application includes the following inventions:

(1) a vascular maturation, normalization or stabilization agent comprising an extract derived from a plant belonging to the genus *Cinnamomum*;

(2) the vascular maturation, normalization or stabilization agent of (1), wherein the extract is derived from a plant of the species *Cinnamomum cassia* Blume;

(3) the vascular maturation, normalization or stabilization agent of (2), wherein the extract is derived from cinnamon twig or cinnamon bark;

(4) the vascular maturation, normalization or stabilization agent of any of (1) to (3), wherein the extract is a water extract;

(5) a Tie-2 activation (phosphorylation) agent comprising an extract derived from a plant belonging to the genus *Cinnamomum*;

(6) the Tie-2 activation (phosphorylation) agent of (5), wherein the extract is derived from a plant of the species *Cinnamomum cassia* Blume;

(7) the Tie-2 activation (phosphorylation) agent of (6), wherein the extract is derived from cinnamon twig or cinnamon bark;

(8) the Tie-2 activation (phosphorylation) agent of any of (5) to (7), wherein the extract is a water extract;
(9) a wrinkle preventer/improver incorporating the vascular maturation, normalization or stabilization agent of any of (1) to (4); and,
(10) a wrinkle preventer/improver incorporating the Tie-2 activation (phosphorylation) agent of any of (5) to (8).

BEST MODE FOR CARRYING OUT THE INVENTION

Plants belonging to the genus *Cinnamomum* are plants of the order Lauraceae, family Lauraceae that consist of more than 300 species, known examples of which include *Cinnamonum cassia* Blume, *C. camphora, C. daphnoides, C. doederleinii, C. japonicum, C. pseudo-pedunculatum, C. sieboldii, C. verum* and *C. zeylanicum*. An extract derived from *Cinnamomum cassia* Blume, and particularly an extract derived from cinnamon twig or cinnamon bark, is preferably used as a vascular maturation, normalization or stabilization agent, Tie-2 activation (phosphorylation) agent or angiogenesis inhibitor in the present invention. Although extracts derived from cinnamon bark are known to be useful as active ingredients of hair tonics, for example (Japanese Unexamined Patent Publication No. H10-265350), they are not known to have vascular maturation, normalization or stabilization activity, Tie-2 activation (phosphorylation) activity, or angiogenesis inhibitory activity.

The aforementioned extracts can be obtained according to ordinary methods by, for example, immersing or hot-refluxing a plant serving as the source thereof with an extraction solvent at room temperature or while heating, filtering and concentrating. Any solvent can be used for the extraction solvent provided it is a solvent ordinarily used for extraction, examples of which include aqueous solvents such as water, physiological saline, phosphate buffer or borate buffer, and organic solvents in the manner of alcohols such as methanol, ethanol, propylene glycol, 1,3-butyleneglycol or glycerin, hydrous alcohols, chloroform, dichloroethane, carbon tetrachloride, acetone, ethyl acetate and hexane, and each of these may be used alone or in combination. Water is preferably used for the solvent. An extract obtained by extracting with the above solvents can be used as is, can be concentrated by freeze-drying, for example, to obtain an extract, can be used after removing impurities as necessary by an adsorption method or by using an ion exchange column, for example, or can be used after eluting with a desired solvent and concentrating after having adsorbed with a porous polymer column (such as Amberlite XAD-2).

Activation of Tie-2 refers to the ability to be able to convert Tie-2 to its active form (phosphorylated Tie-2) by phosphorylation. An example of a Tie-2 activation agent is angiotensin 1, which is known to activate Tie-2.

The vascular maturation, normalization or stabilization agent or Tie-2 activation (phosphorylation) agent of the present invention can be used as a pharmaceutical or cosmetic useful for preventing and improving various diseases and aging caused by changes in vascular structure. The Tie-2 phosphorylation agent of the present invention can be used as a pharmaceutical for improving lesion sites throughout the body accompanying angiogenesis and vascular destruction in various inflammatory diseases, immune diseases and adult-onset diseases, such as various infectious diseases, cancer, rheumatoid arthritis, gout, hypertension, diabetes, arteriosclerosis or atopic dermatitis, by inducing vascular normalization and stabilization. In addition, it can also be used as a pharmaceutical or cosmetic for improving symptoms of edema of organs, including the skin, organ systems and tissues, such as vascular edema caused by inflammatory diseases, immune diseases or adult-onset diseases, or edema and itching caused by increased vascular permeability due to ultraviolet exposure, insect bites or allergies, by inhibiting vascular permeability. Moreover, the Tie-2 phosphorylation agent can be used as a pharmaceutical or cosmetic capable of inhibiting vascular instability by inhibiting cell death of endothelial cells induced by various factors such as inflammatory diseases, immune diseases or adult-onset diseases such as various infectious diseases, cancer, rheumatoid arthritis, gout, hypertension, diabetes, arteriosclerosis, or by inhibiting cell death of endothelial cells caused by radiation injury, various drugs or ultraviolet rays. The Tie-2 phosphorylation agent can be used in pharmaceuticals as an improver of promotion of wound healing such as trauma or decubitus ulcers, vascular maturation in vascular regenerative therapy or ischemic diseases such as cerebral infarction or myocardial infarction, by vascular maturation and dilation of the vascular lumen, and can also be used as an internal medication or externally applied pharmaceutical for lower back pain, frostbite or hair loss by utilizing its circulation improvement effects. It can also be applied to dementia in terms of increasing cerebral blood flow. It can also be used as a cosmetic with respect to hair loss. In addition, in cases of cancer, it can be used as a drug for maintaining stem cells in vitro and in vivo by functioning as a therapeutic drug that induces quiescence in cancer cells.

Photoaging typically refers to changes in appearance and function of skin observed as a result of repeated exposure to sunlight. Ultraviolet light (UV), which is one of the constituent elements of sunlight, and particularly intermediate UV (referred to as UVB and having a wavelength of 290 to 320 nm), is the main cause of photoaging. The exposed dosage of UVB required to cause photoaging is currently unknown. However, repeated exposure to UVB at a level that causes red spots or sunburn normally leads to photoaging. Clinically, photoaging can be identified by skin chapping, wrinkle formation, skin darkening, sag formation, onset of capillary angiectasia, mole formation, onset of purpura, increased injury susceptibility, atrophy, occurrence of fibrous depigmentation regions or the onset of pre-malignant tumors or malignant tumors. Photoaging normally occurs in skin that is routinely exposed to sunlight, such as skin of the face, ears, head, neck and hands. Although photoaging caused by skin damage or exposure to ultraviolet light is the primary cause of aging in skin, the present Tie-2 phosphorylation agent can be used to improve photoaging by inhibiting vascular damage caused by photoaging.

The dosage, administration method and drug form of the vascular maturation, normalization or stabilization agent or Tie-2 phosphorylation agent of the present invention can be suitably determined according to the purpose of use. For example, the administration form of the angiogenesis inhibitor or Tie-2 phosphorylation agent of the present invention may be an oral preparation, parenteral preparation or external preparation and the like. Examples of drug forms include oral preparations such as tablets, powders, capsules, granules, extracts or syrups, parenteral preparations such as injections, intravenous drips or suppositories, and external preparations such as ointments, creams, milky lotions, lotions, facial packs or bath additives.

Although the incorporated amount of the extract derived from a plant belonging to the genus *Cinnamomum* that inhibits angiogenesis of the vascular maturation, normalization or stabilization agent or Tie-2 activation (phosphorylation) agent of the present invention can be suitably determined according to the application, it is typically 0.001 to 20.0% by weight and preferably 0.0001 to 10.0% by weight as dried extract based on the total weight of the inhibitor.

In addition, a vehicle, desiccant, preservative, fortifying agent, thickener, emulsifier, antioxidant, sweetener, sour agent, flavoring agent, colorant or fragrance and the like normally used in foods and pharmaceuticals, or a whitening agent, moisturizer, oily component, ultraviolet absorber, surfactant, thickener, alcohol, powder component, colorant, aqueous component, water or various types of skin nutrients and the like, can be suitably incorporated as necessary in the vascular maturation, normalization or stabilization agent or Tie-2 activation (phosphorylation) agent of the present invention in addition to the extract derived from a plant belonging to the genus *Cinnamomum* described above.

Moreover, in the case of using the vascular maturation, normalization or stabilization agent or Tie-2 activation (phosphorylation) agent of the present invention as an external skin preparation, an assistant commonly used in external skin preparations can be suitably incorporated therein, examples of which include metal chelating agents such as disodium edetate, trisodium edetate, sodium citrate, sodium polyphosphate, sodium metaphosphate or gluconic acid, drugs such as caffeine, tannin, verapamil, tranexamic acid and derivatives thereof, licorice extract, glabridin, hot water extracts of fire thorn (*Pyracantha fortuneana*) fruit, various herbal medicines, tocopherol acetate or glycyrrhizic acid and derivatives or salts thereof, whitening agents such as vitamin C, magnesium ascorbyl phosphate, ascorbyl glucoside, albutin or kojic acid, sugars such as glucose, fructose, mannose, sucrose or trehalose, and vitamin A compounds such as retinoic acid, retinol, retinyl acetate or retinyl palmitate.

EXAMPLES

The following provides a more detailed explanation of the present invention through examples thereof. Furthermore, the present invention is not limited thereto. Incorporated amounts are indicated as percent by weight (wt %).

Preparation of Cinnamon Twig Hot Water Extract Dry Residue 400.7 g of cinnamon twig (branch portion of *Cinnamomum cassia* Blume) were added to 2 L of water followed by heating an extracting for 3 hours and filtering. 2 L of water were added to the resulting residue followed by heating and extracting twice by repeating the same procedure. The resulting liquid was freeze-dried to obtain 39.7 g of a hot water extract dry residue. This sample was used as a cinnamon twig hot water extract.

Treatment of Cinnamon Twig Extract with HP-20 Column 10 g of the hot water extract obtained above were charged into a Diaion HP-20 (Mitsubishi Chemical) column and eluted with hydrous ethanol to obtain a 50% ethanol elution fraction as the target elution fraction.

Preparation of Cinnamon Bark Hot Water Extract Dry Residue 20.12 g of cinnamon bark (bark portion of *Cinnamomum cassia* Blume) were added to 200 ml of water followed by heating and extracting for 3 hours and filtering. 200 ml of water were added to the resulting residue followed by heating and extracting twice by repeating the same procedure. The resulting liquid was freeze-dried to obtain 1.35 g of a hot water extract dry residue. This sample was used as a cinnamon bark hot water extract.

Tie-2 Phosphorylation Evaluation Method

Baf3 cells, a murine pro-B cell line, Ba/F3 transduced with full-length murine TIE2(BaF/TIE2) were incubated in RPMI 1640 medium in the presence of IL-3 (Biosource, PMC0034) and 10% FCS. The cells were plated into a 6-well plate at $2 \times 10^6$ cells/1.5 mL/well and incubated overnight while omitting the FCS starting on the day before cell stimulation. DMSO solutions of the aforementioned hot water extract dry residues, Angiopoietin-1 (R&D System, 932-AN) as a positive control or DMSO as a negative control were added to the wells at a final concentration of 100 ppm, 0.5 ppm and 1000 ppm, respectively, followed by incubating for 10 minutes, cooling the cells on ice and washing with chilled PBS. The cells were then ultrasonically homogenized in RIPA buffer containing protease inhibitors (leupeptin, aprotinin, pepstatin, PMSF, $Na_3VO_4$). Sample buffer (0.2 M Tris-HCl (pH 6.8), 4% SDS, 20% glycerol, 5 mM EDTA, 0.01% BPB) was then added followed by carrying out SDS-PAGE (7.5% polyacrylamide gel, 12 wells, NPU-7.5L, Atto Corp.) under the conditions indicated below.

Gel: 7.5% acrylamide gel (NPU-7.5L, Atto Corp.)
Phoresis conditions: 40 mA (75 minutes, 2 gel sheets)
Tie-2 antibody: sc-324 (Santa Cruz Biotechnology)
Phospho-Tie-2 antibody: #4221 (Cell Signaling)

Next, Western blotting (20 V, 4° C., overnight) was carried out for transcription to a PVDF membrane. After blocking (1 hour) with 5% skim milk/TBST, Tie-2 antibody (Santa Cruz, sc-324) or phosphorylated Tie-2 antibody (Cell Signaling, #4221) was added followed by allowing to stand overnight at 4° C. Next, goat anti-rabbit IgG sHRP (Biosource, ALI3404) was added followed by allowing to stand for 1 hour at room temperature. Protein bands were detected by chemiluminescence detection (ECL).

Figure 1:
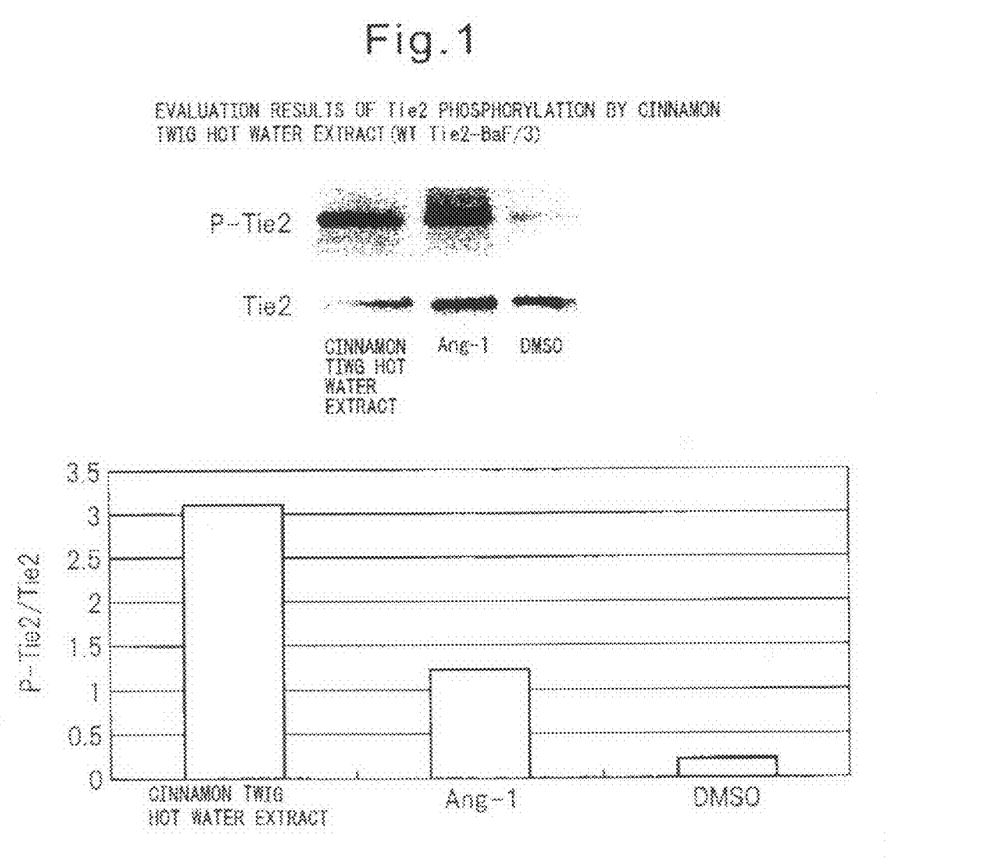
FIG. 1 shows the results of Tie-2 phosphorylation by cinnamon twig extract and Ang-1 in Baf3 cells.
Figure 2:
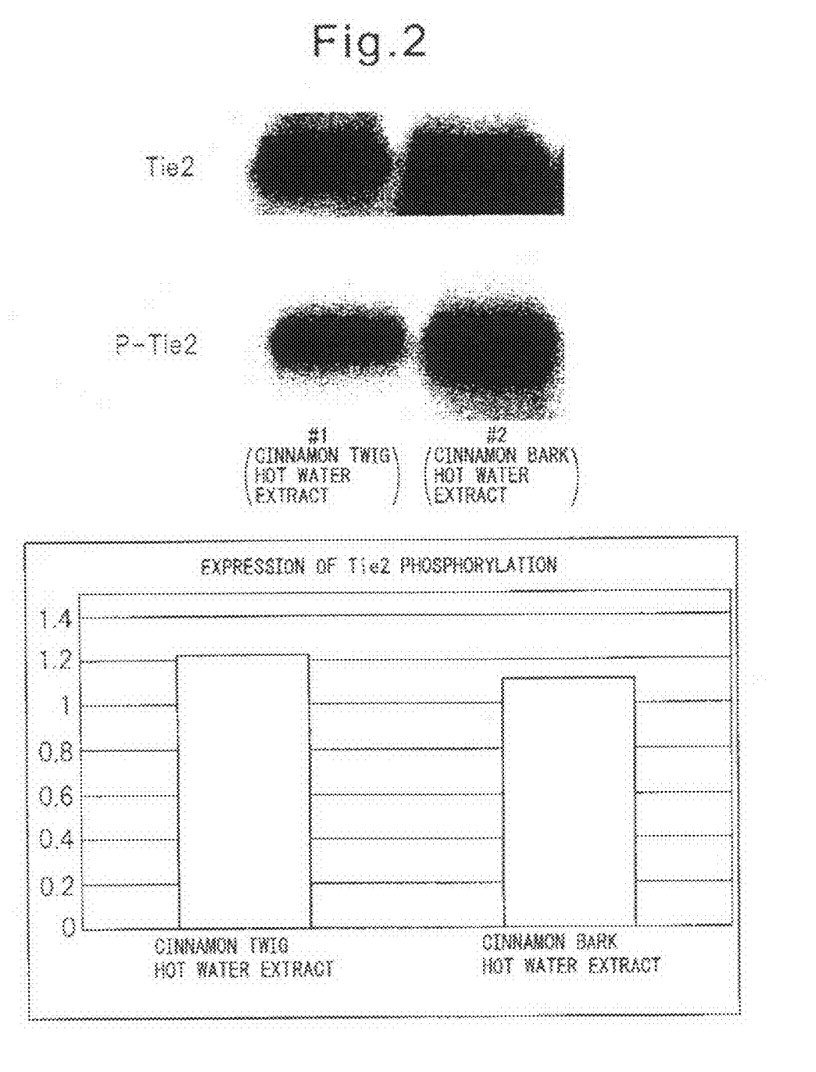
FIG. 2 shows the results of Tie-2 phosphorylation by cinnamon twig extract and cinnamon bark extract.

FIG. 1 shows the results of evaluating Tie-2 phosphorylation of the cinnamon twig hot water extract. The cinnamon twig extract was observed to cause phosphorylation of Tie-2 in the same manner as Ang-1. Thus, the cinnamon twig hot water extract was suggested to demonstrate Tie-2 phosphorylation effects and contribute to vascular maturation, normalization and stabilization, thereby making it possible to inhibit angiogenesis. FIG. 2 shows the results of evaluating Tie-2 phosphorylation of both the cinnamon twig hot water extract and cinnamon bark hot water extract. The cinnamon bark hot water extract was also observed to cause phosphorylation of Tie-2 in the same manner as the cinnamon twig hot water extract.

Figure 3:
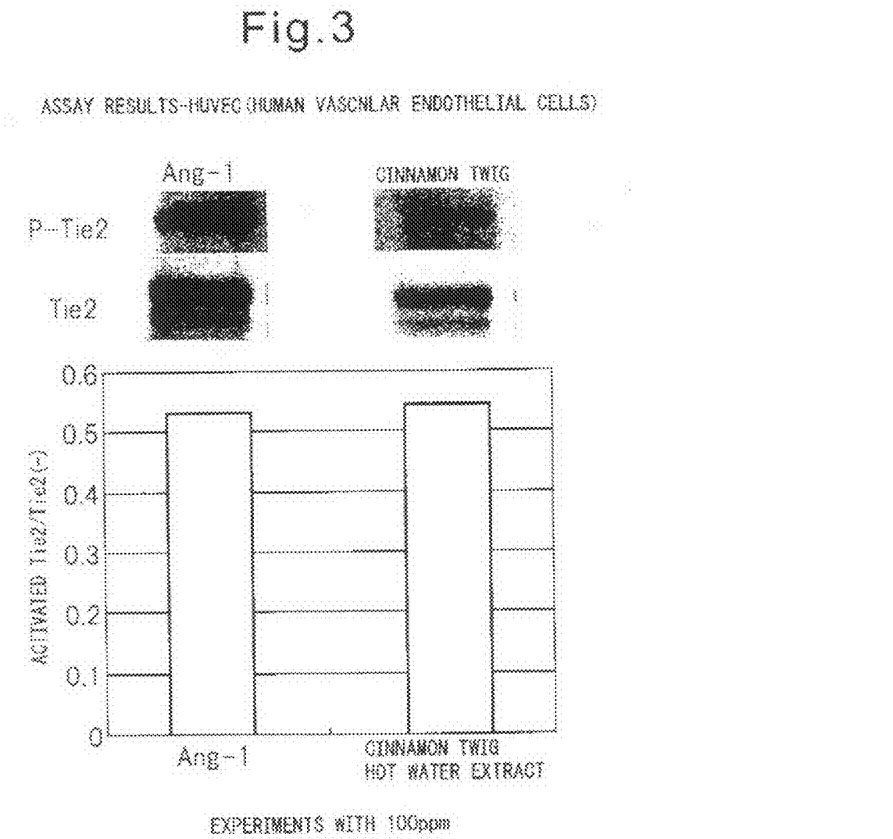
FIG. 3 shows the results of Tie-2 phosphorylation by cinnamon twig extract and Ang-1 in HUVEC cells.

2) Tie-2 phosphorylation was similarly evaluated using normal human umbilical vein endothelial cells (HUVEC). The medium was changed from Humedia to RPMI 1640 three hours before cell stimulation followed by evaluating in the same manner as Baf3 cells. The results are shown in FIG. 3. Similar to the results for Baf3 cells, the cinnamon twig extract caused phosphorylation of Tie-2 in the same manner as Ang-1. Furthermore, significant phosphorylation of Tie-2 was not observed in the system to which DMSO was added that was used as a negative control (not shown).

Test of Wrinkle Prevention/Improvement Effects Photoaging Wrinkle Improvement Test Wrinkles were formed using Hr-1 (Skh-1) hairless mice (Hoshino Laboratory Animals: age 6 to 10 weeks) in compliance with a method consisting of repeatedly irradiating with UVB (Naganuma, M., et al., J. Dermatol. Sci., 25, 29-35, 2001; Schwartz, E., J., Invest. Dermatol., 91, 158-161, 1988) using a partial variation of the method of Schwartz (Haratake, A., et al., J. Invest. Dermatol., 108, 769-775, 1997). Namely, the backs of individual mice were irradiated three times a week for 10 weeks with UVB (light source: Toshiba FL-20SE Fluorescent Lamp, Toshiba). The dosage at the start of the test was set to 36 mJ/cm$^2$ and was gradually increased starting in the 2nd week, eventually reaching a dosage of 216 mJ/cm$^2$ in the 10th week. The total radiation dosage was 4.6 J/cm$^2$. Values measured using a UV radiometer (UVR-305/365D (II), Topcon) were used for radiation dosage. Following completion of radiation exposure, photographs of the backs of the animals were taken, the degree of wrinkle formation was scored in accordance with the following evaluation criteria using a partial variation of the method of Bissett (Bissett, D. L., et al., Photochemistry and Photobiology, 46, 367-378, 1987), and the extract of Example 1 (cinnamon twig extract, incorporating the aforementioned hot water extract dry residue) or the extract of Example 2 (cinnamon twig extract, incorporating 50% ethanol elution fraction of HP-20 column) was applied only to those animals that demonstrated wrinkle formation scored to 7 or higher. Scoring of wrinkle formation was carried out separately by three analysts and final scores were determined through mutual consent.

Furthermore, evaluation of wrinkle formation was carried out on the basis of a protocol that was approved by an in-house laboratory animal screening committee while strictly observing the Law for Humane Treatment and Management of Animals and other related ordinances.

Composition of Example 1

| (Components) | Incorporated Amt. (wt %) |
| --- | --- |
| Cinnamon twig extract | 1.0 |
| Cosmetic quality alcohol | 30.0 |
| Purified water | Balance |

Composition of Example 2

| (Component) | Incorporated Amt. (wt %) |
| --- | --- |
| 50% ethanol elution fraction of HP-20 column | 1.0 |
| Cosmetic quality ethanol | 30.0 |
| Purified water | Balance |

Scoring: Evaluation Criteria
0: No wrinkles observed
1: wrinkles shallower, shorter or fewer than level 2
2: Shallow wrinkles observed
3: Wrinkles deeper or longer than level 2, but shallower, shorter or fewer than level 4
4: Shallow wrinkles observed over entire back
5: Wrinkles deeper or longer than level 4, but shallower or shorter than level 6
6: Deep wrinkles observed
7: Wrinkles deeper, longer and more numerous than level 6, but shallower or shorter than level 8
8: Deep, long wrinkles observed over entire back Hairless mice evaluated as a score of 7 or higher were divided into two groups of 5 animals each so that both groups had the same average score, and the 100 μl of the formulations of Example 1 and Example 2 having the compositions described above were respectively applied to the skin of the entire backs of the animals of each group once a day and 5 times a week for 6 consecutive weeks.

Following completion of application, photographs of the backs of the animals were taken and the degree of wrinkle formation was separately scored by 3 analysts in accordance with the previously indicated evaluation criteria while concealing the group name of the animals, after which the final scores were determined through mutual consent.

In addition, the same testing was carried out on animals using a formulation designated as Comparative Example 1 from which the cinnamon twig extract had been omitted from the composition of Example 1.

Composition of Comparative Example 1

| (Components) | Incorporated Amt. (wt %) |
| --- | --- |
| Cosmetic quality ethanol | 30.0 |
| Purified water | Balance |

The degree of wrinkle improvement was determined in the manner described below. Namely, the degree of improvement was calculated according to the following equation:

Degree of wrinkle improvement=(Score prior to applying sample solution)−(score after applying sample solution for 6 weeks)

The degrees of improvement as obtained according to the above equation are shown as the average value of each group in the table below.

TABLE 1

|  | Degree of wrinkle improvement Average |
| --- | --- |
| Cinnamon twig extract | 3.2 |
| Control formulation | 2.3 |
| Cinnamon twig HP20 column 50% ethanol elution fraction | 2.4 |
| Control formulation | 1.4 |

As is clear from the table, wrinkle reduction was significantly promoted in the group to which was applied the formulation of Example 1 of the present invention (incorporating cinnamon twig extract) as compared with the group to which was applied the control formulation (not incorporating extract). Similarly, wrinkle reduction was also significantly promoted by Example 2. On the basis of these results, both the cinnamon twig solution and the cinnamon twig HP-20 column 50% ethanol elution fraction were confirmed to demonstrated wrinkle improving effects.

Evaluation of Angiogenesis Inhibitory Action

A test was conducted for confirming the angiogenesis inhibitory action of cinnamon bark hot water extract.

Figure 5:
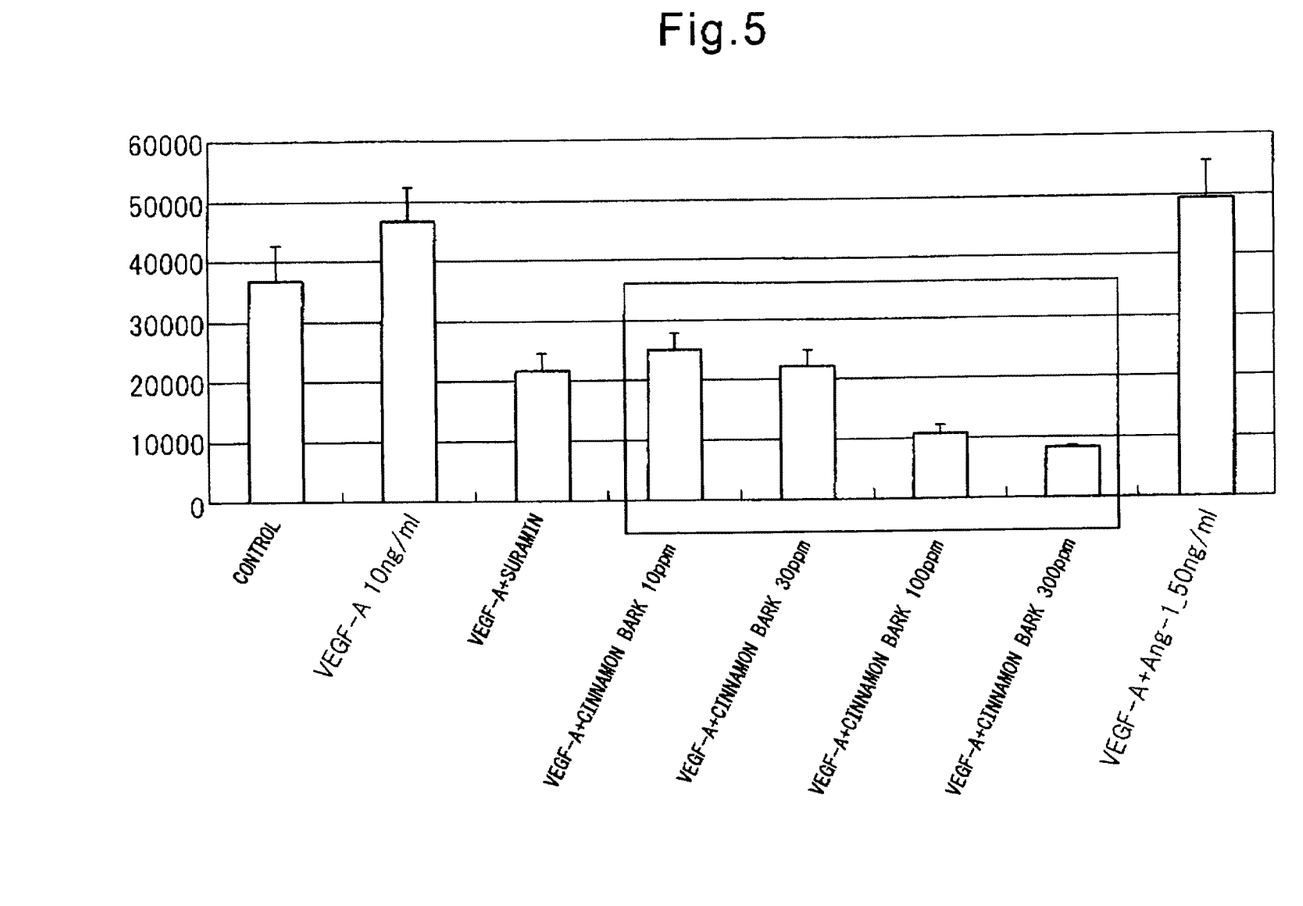
FIG. 5 shows the angiogenesis inhibitory action of cinnamon extract based on the length of lumen formation.
Figure 6:
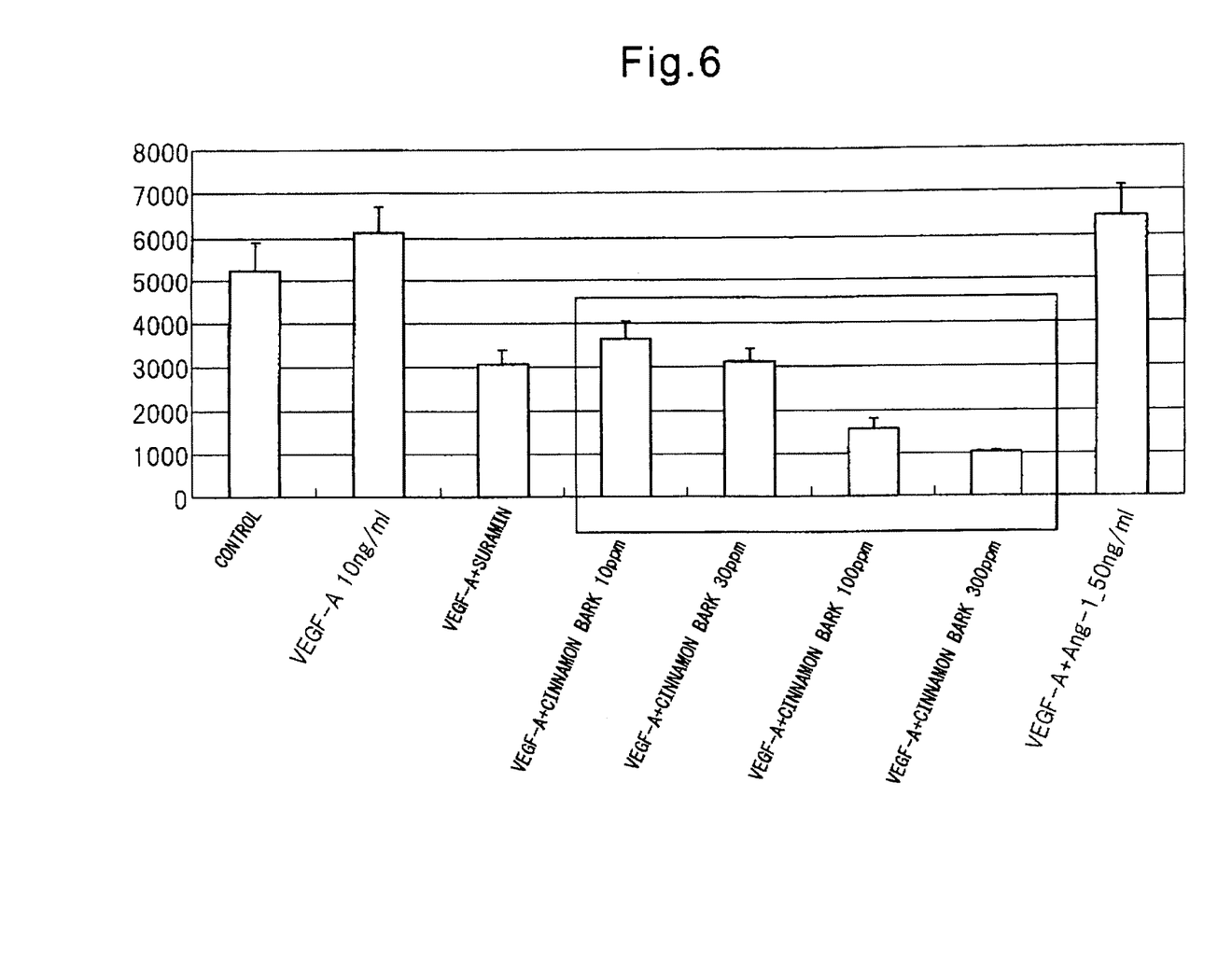
FIG. 6 shows the angiogenesis inhibitory action of cinnamon extract based on the surface area of lumen formation.

Normal human umbilical vein endothelial cells and normal human dermal fibroblasts were co-cultured at a constant ratio using an angiogenesis kit (Kurabo Industries) and prepared in the growth state of the initial stage of lumen formation. The cells were incubated (under conditions of 37° C. and 5% $CO_2$) after adding medium containing a prescribed concentration of cinnamon bark hot water extract in the presence of 10 ng/ml of vascular endothelial cell growth factor A (VEGF-A, Kurabo Industries). The medium was respectively replaced with medium containing a prescribed concentration of cinnamon bark extract in the presence of VEGF-A at 4 days, 7 days and 9 days after the start of culturing. Subsequently, the cell layer in each well was fixed with 70% ethanol and stained with CD31 (PECAN-1). The stained images obtained from each well were then photographed (FIG. 4), and the images were analyzed using the length and surface area of lumen formation as indicators to evaluate angiogenesis inhibitory action (FIGS. 5 and 6). Image analysis for the length of lumen formation and image analysis for surface area were respectively carried out using angiogenesis quantification software (Kurabo Industries). Increases in the length of lumen formation and increases in the surface area of lumen formation were taken to mean that angiogenesis was observed. A group to which only the medium was added was used as a control, a group to which only VEGA-A (10 ng/ml) was added was used as a negative control, and a group to which was added Suramin, a known angiogenesis inhibitor, was used as a positive control. Moreover, angiogenesis inhibitory action in the presence of VGF-A was also evaluated for Ang-1, which is known to have an action that is responsible for vascular stabilization.

Discussion of Results

Figure 4:
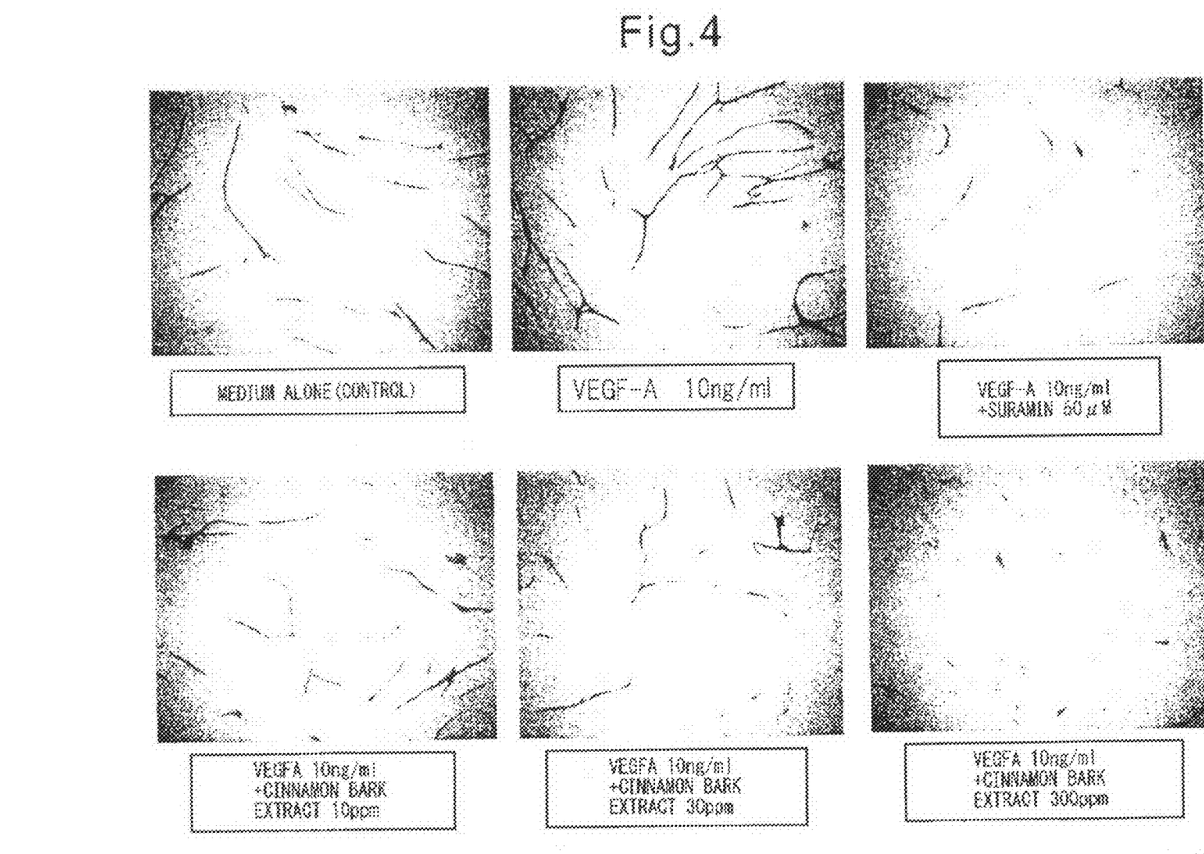
FIG. 4 shows a stained image of lumen formation.

FIG. 4 is a stained image of lumen formation following staining of the cells with DAB. In contrast to lumen formation being observed in the case of having cultured in the presence of VEGF-A, lumen formation was determined to be inhibited in the case of culturing with VEGF-A in the presence of a known angiogenesis inhibitor in the form of Suramin and cinnamon bark extract (and particularly at 300 ppm). FIGS. 5 and 6 show the results of quantifying the results observed in FIG. 4, and suggested that cinnamon bark extract significantly inhibits angiogenesis induced by VEGF-A dose-dependently between 10 and 300 ppm. It is interesting to note that Ang-1 did not have angiogenesis inhibitory action. Thus, it was suggested that, although cinnamon bark hot water extract demonstrates actions such as vascular stabilization action by phosphorylating Tie-2 by an Ang-1-like mechanism, it demonstrates angiogenesis inhibitory action by a mechanism that differs from that of Ang-1.

The invention claimed is:

1. A method of maturing, normalizing or stabilizing blood vessels in the skin of a subject in need thereof, comprising the step of applying to said skin a composition comprising an effective amount of a water extract of *Cinnamomum cassia* Blume, wherein the blood vessels are affected by photoaging, wherein the composition comprises 0.001% to 20% by weight of said water extract, and wherein the composition is applied to said skin repeatedly and within a time period that is close enough in time to the subject's exposure to sunlight to mature, normalize or stabilize the subject's blood vessels against photoaging.

2. The method according to claim 1, wherein the extract is derived from cinnamon twig or cinnamon bark.

3. A method of reducing and/or improving wrinkles in the skin of a subject in need thereof, comprising the step of applying to said skin a composition comprising an effective amount of a water extract of *Cinnamomum cassia* Blume, wherein the wrinkles are caused by photoaging, wherein the composition comprises 0.001% to 20% by weight of said water extract, and wherein the composition is applied to said skin repeatedly and within a time period that is close enough in time to the subject's exposure to sunlight to reduce and/or improve the subject's wrinkles against photoaging.

4. The method according to claim 3, wherein the extract is derived from cinnamon twig or cinnamon bark.

* * * * *